(12) United States Patent
Walsh et al.

(10) Patent No.: US 12,090,056 B2
(45) Date of Patent: Sep. 17, 2024

(54) MULTI-STAGE ADDITIVE MANUFACTURING PROCESS WITH INSERTS

(71) Applicant: Howmedica Osteonics Corp., Mahwah, NJ (US)

(72) Inventors: Gearoid Walsh, Ennis (IE); Mark Lehane, Glounthaune (IE)

(73) Assignee: Howmedica Osteonics Corp., Mahwah, NJ (US)

( * ) Notice: Subject to any disclaimer, the term of this patent is extended or adjusted under 35 U.S.C. 154(b) by 1079 days.

(21) Appl. No.: 16/944,810

(22) Filed: Jul. 31, 2020

(65) Prior Publication Data

US 2021/0030545 A1 Feb. 4, 2021

Related U.S. Application Data

(60) Provisional application No. 62/881,561, filed on Aug. 1, 2019.

(51) Int. Cl.
| | |
|---|---|
| *A61F 2/30* | (2006.01) |
| *B29C 65/56* | (2006.01) |
| *B33Y 10/00* | (2015.01) |
| *B33Y 80/00* | (2015.01) |
| *A61B 17/00* | (2006.01) |
| *A61B 17/80* | (2006.01) |
| *B22F 10/28* | (2021.01) |

(52) U.S. Cl.
CPC .......... *A61F 2/3094* (2013.01); *B29C 65/565* (2013.01); *B33Y 10/00* (2014.12); *B33Y 80/00* (2014.12); *A61B 2017/00526* (2013.01); *A61B 17/80* (2013.01); *A61F 2002/30331* (2013.01); *A61F 2002/30405* (2013.01); *A61F 2002/30733* (2013.01); *A61F 2002/30784* (2013.01); *A61F 2002/30957* (2013.01); *A61F 2002/30985* (2013.01); *B22F 10/28* (2021.01)

(58) Field of Classification Search
CPC ...... A61F 2/30; A61F 2/32; A61F 2/08; A61F 2/40; A61F 2002/0847; A61F 2/3094; B33Y 10/00; B33Y 80/00
See application file for complete search history.

(56) References Cited

U.S. PATENT DOCUMENTS

| | | | |
|---|---|---|---|
| 7,537,664 | B2 | 5/2009 | O'Neill et al. |
| 8,728,387 | B2 | 5/2014 | Jones et al. |
| 8,735,773 | B2 | 5/2014 | Lang |
| 9,135,374 | B2 | 9/2015 | Jones et al. |
| 9,180,010 | B2 | 11/2015 | Dong et al. |
| 9,456,901 | B2 | 10/2016 | Jones et al. |
| 9,629,725 | B2 | 3/2017 | Lubensky et al. |
| 9,750,850 | B2 | 9/2017 | Fonte et al. |
| 9,949,837 | B2 | 4/2018 | Wang et al. |
| 9,993,341 | B2 | 6/2018 | Vanasse et al. |

(Continued)

OTHER PUBLICATIONS

Extended European Search Report including Written Opinion for EP20188981.3 issued Jan. 12, 2021; 8 pages.

*Primary Examiner* — Jason-Dennis N Stewart
(74) *Attorney, Agent, or Firm* — Lerner David LLP

(57) ABSTRACT

According to one aspect of the disclosure, a method of manufacturing an implant may comprise manufacturing a first portion, coupling an insert with the first portion to form a combined first portion and insert assembly, and additively manufacturing a second portion on the assembly after the coupling step.

11 Claims, 10 Drawing Sheets

(56) References Cited

U.S. PATENT DOCUMENTS

| | | |
|---|---|---|
| 10,099,290 B2 | 10/2018 | Lacy et al. |
| 10,154,913 B2 | 12/2018 | Steinmann et al. |
| 2006/0147332 A1 | 7/2006 | Jones et al. |
| 2013/0072988 A1 | 3/2013 | Hulliger |
| 2016/0089191 A1 | 3/2016 | Pak et al. |
| 2017/0056134 A1 | 3/2017 | Cordonnier |
| 2017/0095887 A1 | 4/2017 | Marchione et al. |
| 2018/0272460 A1 | 9/2018 | Nelson et al. |
| 2018/0296343 A1 | 10/2018 | Wei |
| 2018/0338838 A1 | 11/2018 | Cryder et al. |
| 2019/0117375 A1* | 4/2019 | Snedeker .............. A61F 2/0811 |
| 2019/0184058 A1* | 6/2019 | Aihara ................... A61L 27/06 |
| 2020/0268425 A1* | 8/2020 | Ballard ................. B33Y 80/00 |

\* cited by examiner

MULTI-STAGE ADDITIVE MANUFACTURING PROCESS WITH INSERTS

CROSS-REFERENCE TO RELATED APPLICATIONS

The present application claims the benefit of the filing date of U.S. Provisional Patent Application No. 62/881,561 filed Aug. 1, 2019, the disclosure of which is hereby incorporated herein by reference

BACKGROUND OF THE INVENTION

Additive manufacturing is a type of 3D printing where products are capable of being fabricated with custom geometries by means of sequentially adding layers of material. This method of manufacturing is a viable alternative to traditional manufacturing processes such as computer numerical control ("CNC") machining as additive manufacturing allows for greater customization and control in printing parts, especially parts that would be difficult to manufacture via traditional means (e.g., porous parts).

However, additive manufacturing is not without its limitations. For instance, current practices of additive manufacturing are generally unable to replicate the high degree of surface smoothness that is possible via a machining process. Thus, products manufactured via additive manufacturing often require post processing, such as media or polishing technologies, which can be difficult and cannot be localized. In addition, additive manufacturing is generally unable to achieve the fine levels of tolerance that can be achieved via different manufacturing approaches.

Therefore, there is a need for an improved manufacturing process to produce components that are difficult to manufacture via traditional forms of manufacturing, such as porous structures and the like, while also mitigating certain manufacturing limitations of additive manufacturing, such as those mentioned above.

BRIEF SUMMARY

The present disclosure is directed to a method of manufacturing that leverages the strengths of various manufacturing means to produce an orthopedic implant that includes complex structures, such as porous structures, and structures with tight tolerances, such as bone fastener openings.

According to one aspect, the disclosure includes a method of manufacturing an implant may comprise manufacturing a first portion, coupling an insert with the first portion to form a combined first portion and insert assembly, and additively manufacturing a second portion on the assembly after the coupling step. Further, the method may include separately manufacturing the insert from the first portion via one of machining, molding, casting, and forging. Further, coupling the insert with the first portion may include inserting the insert into a bore of the first portion by one of press-fit and threading. Further, the second portion may comprise a porous structure having a porosity of 10% to 90%. Further, the first portion may comprise a solid structure. Further, manufacturing the first portion may include additively manufacturing the first portion on a build plate, and the method further comprises removing the first portion from the build plate prior to coupling the insert to the first portion. Further, the method may include placing the combined first portion and insert assembly onto the build plate prior to the step of additively manufacturing the second portion. Further, manufacturing the first portion may include additively manufacturing the first portion on the build plate such that the first portion occupies a first position on the build plate, and the placing step includes placing the first portion and insert assembly in the first position on the build plate. Further, additively manufacturing the first portion may be performed on a build plate located at a first location, and the method further comprises transporting the build plate including the first portion thereon from the first location to a second location, the coupling step being performed at the second location. Further, additively manufacturing the second portion may be performed over at least a portion of the insert such that the insert is at least partially disposed beneath the second portion thereby securing the insert to the first portion.

In another aspect, the disclosure includes a method of manufacturing an implant may comprise manufacturing a base having a plurality of bores extending therein, inserting an insert into each of the bores of the base, and additively manufacturing a section on the base after the inserting step. Further, the method may include machining the inserts from a blank of raw material prior to the inserting step. Further, inserting the inserts into the base may include installing the inserts into a corresponding bore of the base by one of press-fit and threading. Further, the inserting step may include inserting each insert into a corresponding bore such that an edge of each insert is flush with, or recessed below, a top surface of the base. Further, manufacturing the section may be performed over at least a portion of each insert such that each insert is at least partially disposed beneath the section thereby securing each insert within their respective bore. Further, the section may comprise a porous structure having a porosity of 10% to 90%. Further, manufacturing the base may include additively manufacturing the base on a build plate and the method further comprises removing the base from the build plate before the inserting step. Further, the method may further comprise placing a combined base and insert assembly onto the build plate after the inserting step.

In another aspect, the disclosure includes an implant may comprise a base having an inner surface defining a bore and a ledge extending from the inner surface, an insert received within the bore and adjacent the ledge, and a section integrally connected to the base via an additive manufacturing process and at least partially overlapping the insert such that the insert is trapped between the ledge on a surface of the base, the section having porous and non-porous sections. Further, the insert may include an inner surface at least partially defining a bone fastener opening and at least one projection extending inwardly from the inner surface.

BRIEF DESCRIPTION OF THE DRAWINGS

These and other features, aspects, and advantages of the present invention will become better understood with regard to the following description, and accompanying drawings where.

DETAILED DESCRIPTION

Many orthopedic implants utilize one or more means for securing the implant to bone. For example, porous structures may comprise a bone facing surface which allows bone to grow into the porous structure to provide long-term fixation of the implant. Implants may also deploy other fixation means, such as bone fasteners which are used to secure the implant to the bone. Such bone fasteners may be used in conjunction with porous structures such that the bone fasteners provide immediate fixation while the porous structures facilitates additional long-term fixation via bone growth therein. Porous structures are optimally built via additive manufacturing as the layer-by-layer nature of additive manufacturing allows for the creation of pores and complex three-dimensional structures that simply could not be achieved via traditional manufacturing processes. Implants that also utilize bone fasteners typically have corresponding bone fastener openings that allow for the fastener to be passed therethrough and into the underlying bone. However, bone screw openings are generally defined by smooth surfaces that have tolerances relative to the bone fastener that are tighter than can be easily achieved using additive manufacturing.

The present disclosure describes a method of manufacturing that leverages the strengths of various manufacturing means to produce an orthopedic implant that includes complex structures, such as porous structures, and structures with tight tolerances, such as bone fastener openings. FIGS. 1-5B depict an exemplary implant 100 that can be produced via such manufacturing method. Implant 100 is a baseplate of a reverse shoulder prosthesis and generally includes a base or first section 200, inserts 300, and a second section 500. Implant 100 is one embodiment which can be made by the method of manufacture described in further detail below. However, it should be understood that other implants can be manufactured via the method disclosed herein, such as a tibial baseplate, acetabular cup component, bone augment (e.g., the Restoration Acetabular Wedge Augment by Howmedica Osteonics Corp. of Mahwah, NJ), and the like, for example.

Figure 1:
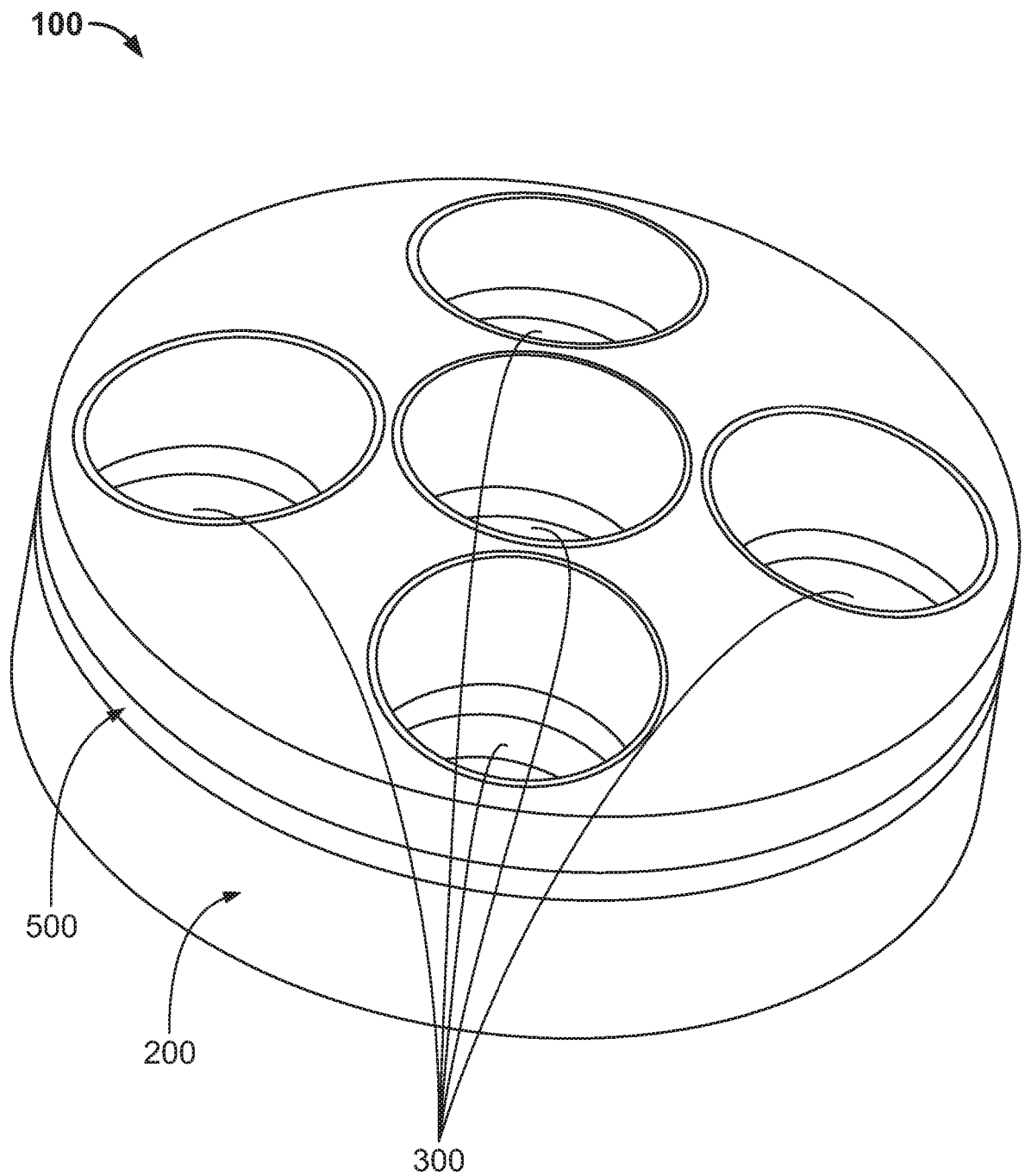
FIG. 1 is a perspective view of an implant according to one embodiment of the present invention.
Figure 2:
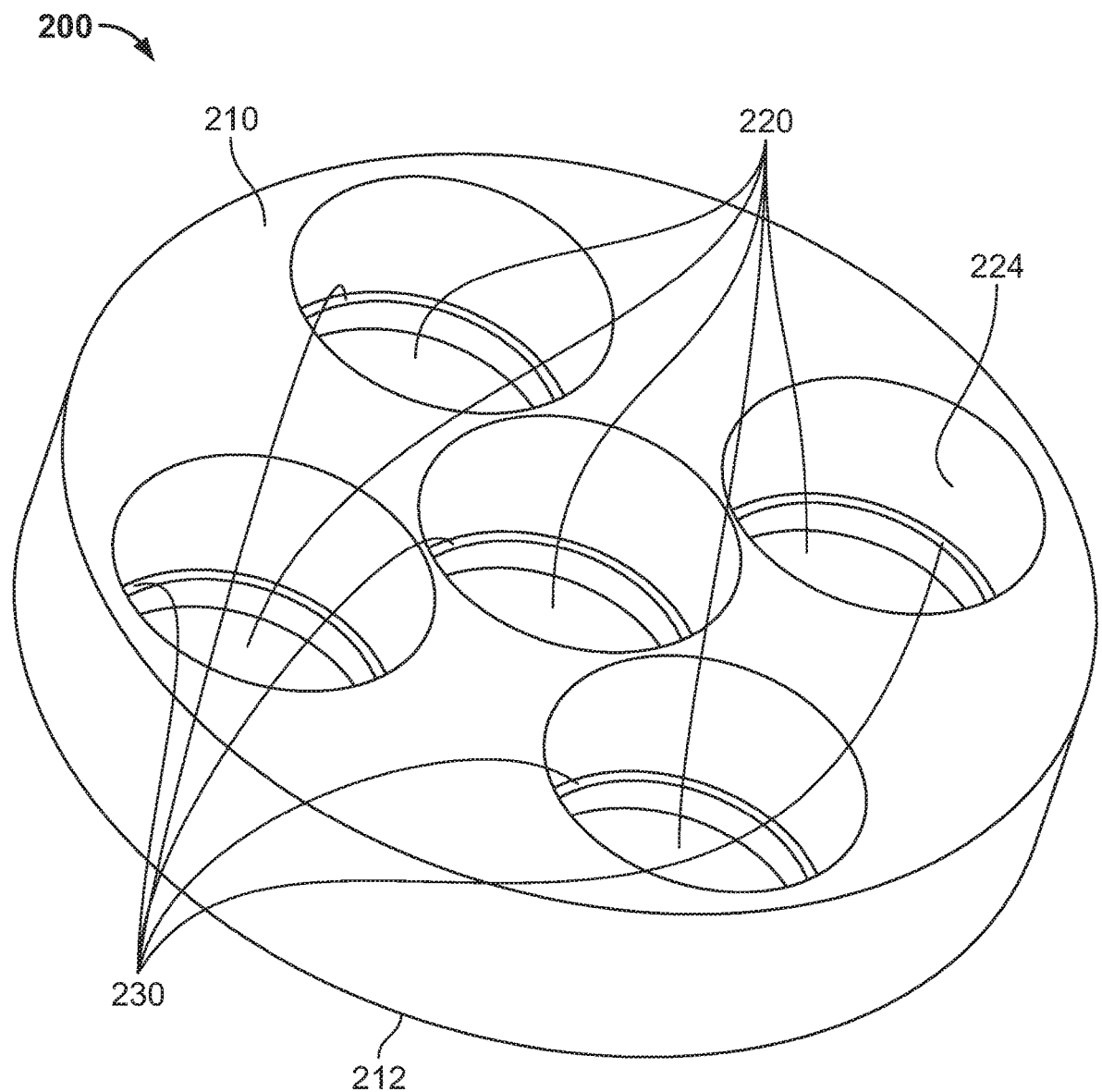
FIG. 2 is a perspective view of a base of the implant of FIG. 1.

FIG. 2 depicts base 200 which has a first surface 210, second surface 212, bores 220, and ledges or shoulders 230. Base 200 has a cylindrical shape and five circular bores 220 of equal diameter extending from first surface 210 through base 200. However, in some embodiments, such bores 220 have differing diameters and may have differing trajectories such that bores 220 extend through base 200 at different angles. There is one bore 220 in the center of base 200, and four other bores 220 equally and concentrically spaced about center bore 220. However, in other embodiments, more or less bores 220 than that depicted may be differently arranged. Ledges 230 extend inwardly a distance from the interior surface 224 of bores 220 and have a face that faces toward first surface 210.

Although base 200 is cylindrical in shape, it is envisioned in other embodiments that the base 200 may also be of any shape (e.g., cuboid, pyramidal, or the like.). In yet other embodiments, it is envisioned that base 220 may include any number of bores 220 (e.g., one, two, or three bores.). In yet other embodiments, it is envisioned that bores 220 may be of any shape (e.g. rectangular, triangular, or the like). In yet other embodiments, it is envisioned that surfaces 210 and/or 212 may be concave or convex. In yet other embodiments, it is envisioned that the interior surface 224 of bores 220 may have threads. Base 200 may also constitute a solid structure such that its inherent porosity precludes bone ingrowth therein. Such solid structure provides strength to implant 100. However, base 200 can include a porous structure therein, as desired. As described further below, base 200 may be manufactured via additive manufacturing or via other means such as machining, forging, casting, or injection molding, for example.

Figure 3A:
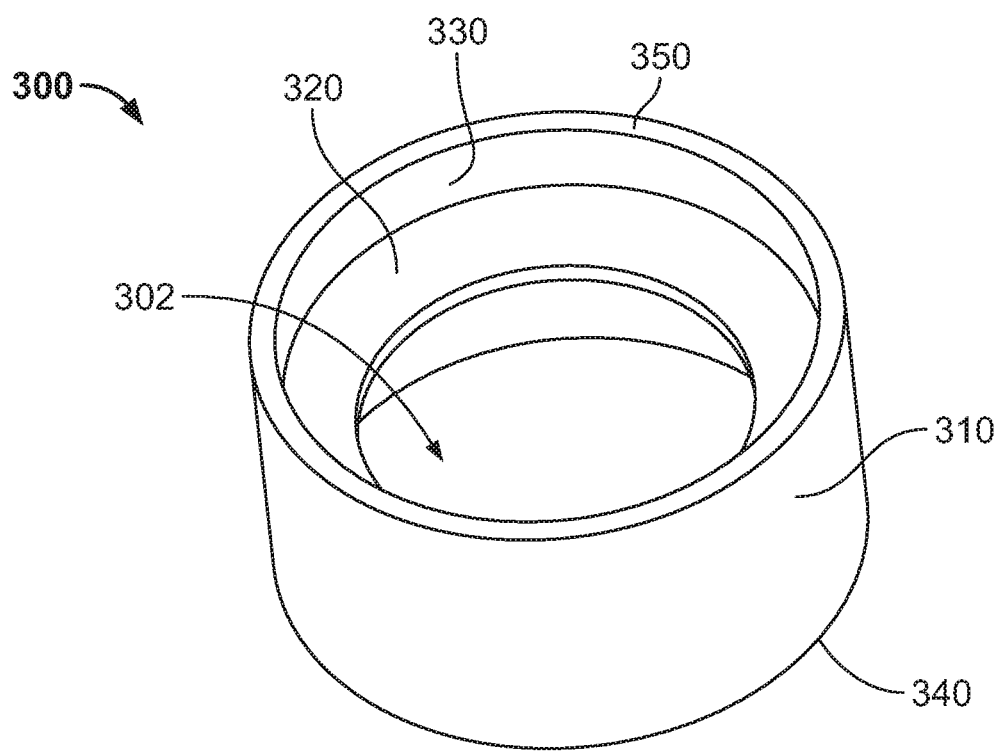
FIG. 3A is a perspective view of an insert of the implant of FIG. 1.
Figure 3B:
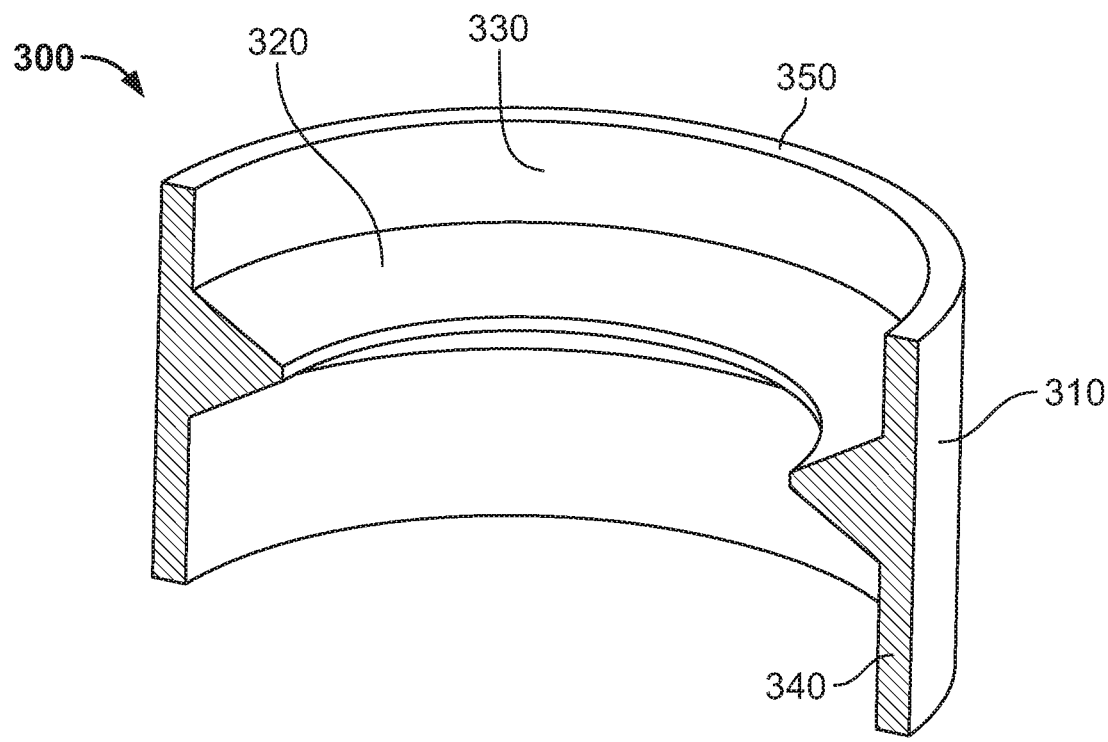
FIG. 3B is a cross-sectional view of the insert of the implant of FIG. 3A taken along a midline thereof.

FIGS. 3A and 3B depict insert 300 which has an exterior surface 310, protrusion or lip 320, interior surface 330, first edge 340, and second edge 350. Insert 300 is configured to be securely received within bore 220 of base 200 such that exterior surface 310 lies flush with the interior surface of bore 220 and first edge 340 sits on ledge 230. Protrusion 320 is pyramidal and extends inwardly from interior surface 330. In addition, protrusion 320 extends circumferentially about a longitudinal axis of insert 300. Protrusion 320 and interior surface 330 define a bone fastener opening 302 of insert 300 while protrusion 320 defines the narrowest part of opening 302. Protrusion 320 may be made from an alloy, such as a titanium alloy, that has a hardness less than that of a bone fastener (not shown) that passes therethrough. In this regard, the bone fastener may be passed through opening 302 at a multitude of different angles and may deform protrusion 320 therein so as to obtain firm purchase with insert 320 despite the insertion angle. Alternatively, protrusion 320 may be a thread that engages threads of the bone fastener to guide the bone fastener at a predefined angle into the bone. Regardless, the tolerances between each bore 220 and the selected bone fastener are preferably tight to ensure such purchase and to help prevent unintended backing out of the bone fastener. For example, the tolerances may be +/−0.005 mm (0.0002") or less.

Although insert 300 is depicted as cylindrical in shape, it is envisioned that, in other embodiments, insert 300 may be any shape (e.g., rectangular) that corresponds to the shape of bore 220 of base 200. It is also envisioned that exterior surface 310 may have projections or fins extending therefrom to mate with corresponding recesses or grooves in base 200 to prohibit rotation of insert 300 relative to base 200 when received therein. In yet other embodiments, it is envisioned that protrusion 320 may be any shape (e.g., rectangular) that allows the screw, or other bone anchoring device, to lie flush within the interior of the insert. Moreover, protrusion may be interrupted so as to form a plurality of protrusions in one or more rows of protrusions that extend inwardly from interior surface 330, such as, for example, the lips disclosed in U.S. Pub. No. 2016/0089191, the disclosure of which is hereby incorporated by reference herein in its entirety. In yet other embodiments, it is envisioned that exterior surface 310 may have a set of threads corresponding to threads within bore 220 such that insert 300 may be secured to base 200 by being threadably received within base 200. Alternatively, each insert 300 may be slightly larger than its respective bore 220 such that insert can be press-fit therein.

Figure 4:
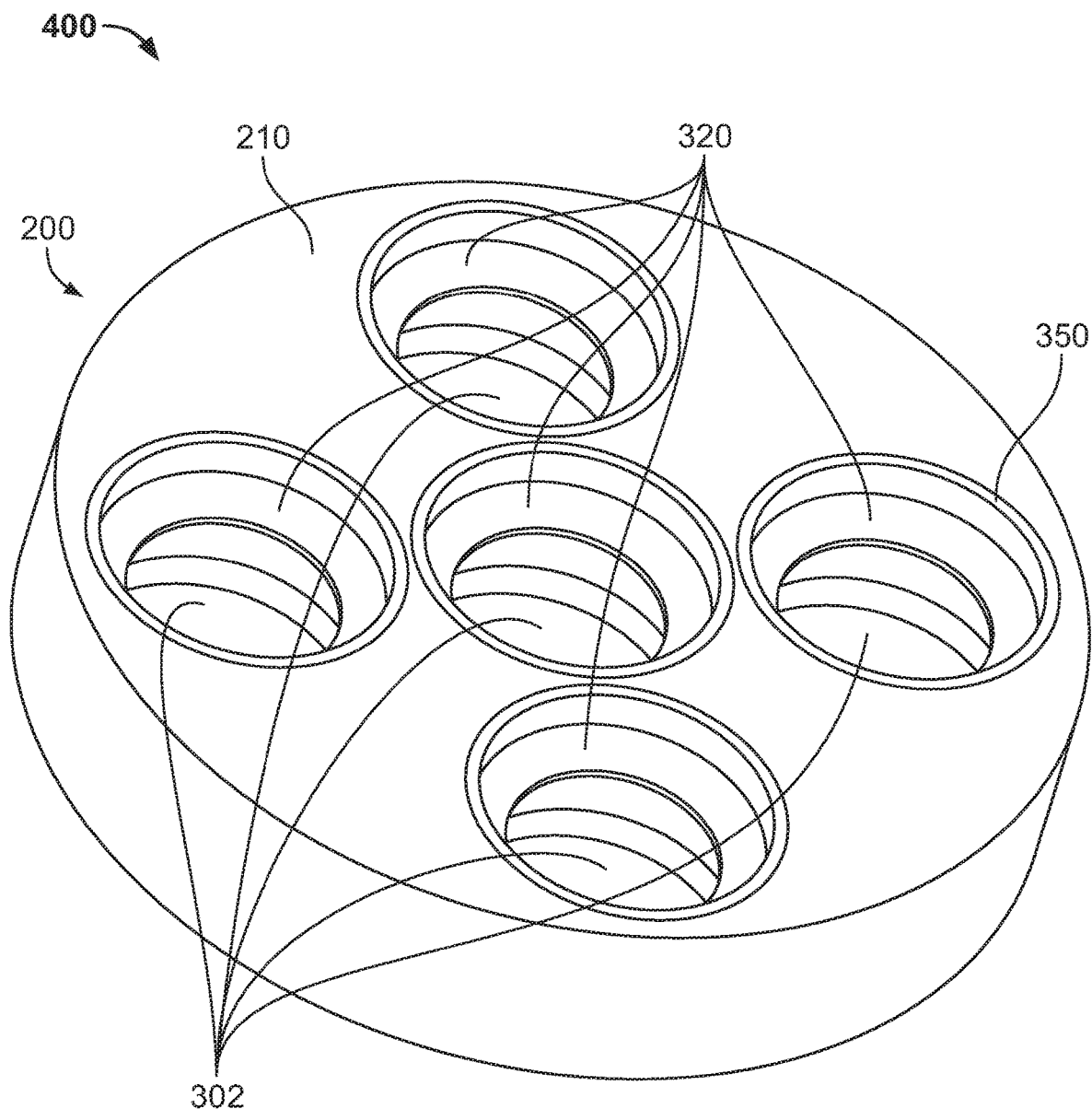
FIG. 4 is a perspective view of a partial-assembly of the implant of FIG. 1.

FIG. 4 depicts assembly 400. Assembly 400 includes base 200 after inserts 300 have been inserted within bores 220. Inserts 300 may be secured by, for example, press-fit, snap-fit, being threaded, welded, or the like. Moreover, as mentioned above, inserts 300 are inserted such that first edge 340 abuts ledge 230 within a respective bore 220. In addition, second edge 350 preferably lies flush with first surface 210 of base 200, as shown. This allows cap 500 to be secured on top of base 200 via an additive manufacturing process, as described below. However, in some embodiments, edge 350 may be recessed beneath first surface 210.

Figure 5A:
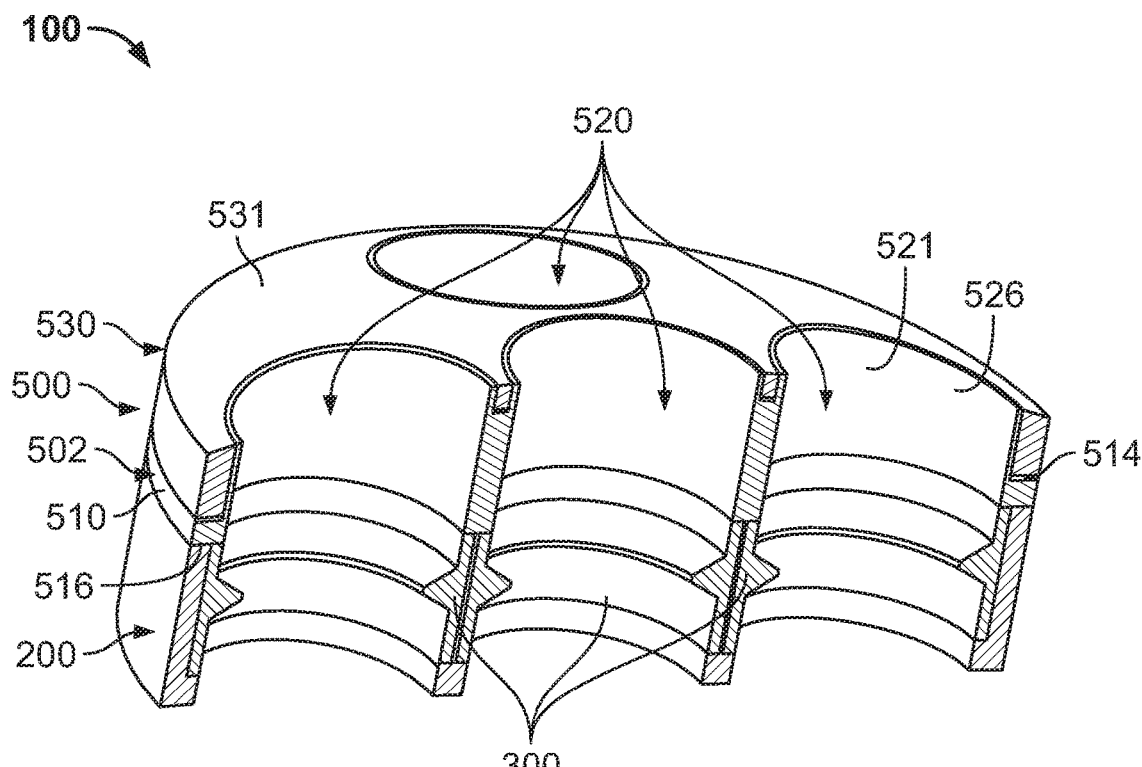
FIG. 5A depicts a perspective, cross-sectional view of the implant of FIG. 1 taken along a midline thereof.

FIG. 5A depicts a cross-sectional, perspective view of implant 100, including second section 500. Second section 500 includes a non-porous section or cap 502 and a porous section or crown 530. Cap 502 is a solid non-porous section which includes a plate or rim member 510 and hollow cylindrical members 520. Cylindrical members 520 are joined to and extend away from plate member 510. In addition, cylindrical members 520 are joined to each other at sides thereof. However, cylindrical members 520 are not connected to each other along their entire lengths such that a recess 524 is formed between cylindrical members 520 at terminal or proximal ends 521 thereof. Crown 530 has a porous structure and is formed atop of plate member 510 and fills in spaces about cylindrical members 520 including recesses 524. Such porous crown 530 forms an end surface 531 of device 100 which is flush with terminal ends 521 of cylindrical members 520.

Plate member 510 is generally circular to match the profile of first section 200 and includes a top or first surface 514 and bottom or second surface 516. Cap 502 is attached to base 200 and inserts 300 such that second surface 516 of plate member 510 is connected to second edge 350 and first surface 210 of inserts 300 and base 200, respectively, of the assembly 400 after inserts 300 have been secured within bores 220 of base 200. In this regard, when assembled, cylindrical members 520 are extensions of inserts 300 and each have an interior surface 526 that is flush with an interior surface 224 of a corresponding insert 300. Cap 502 may be secured to assembly 400 via additive manufacturing, as described below, such that cap 502 is sintered, melted, or the like to base 200 and inserts 300. Alternatively, cap 502 can be connected to assembly 400 via conventional techniques, such as welding, such as sonic welding, or the like. However, cap 502 is preferably connected to assembly 400 and formed via additive manufacturing as cap 502 can be formed concurrently with crown 530 in a layer-by-layer manner, as described below. In this manner, inserts 300 are locked within implant 100 at least by being seated between ledges 230 and bottom surface 516, as best shown in FIGS. 5A and 5B.

Figure 5B:
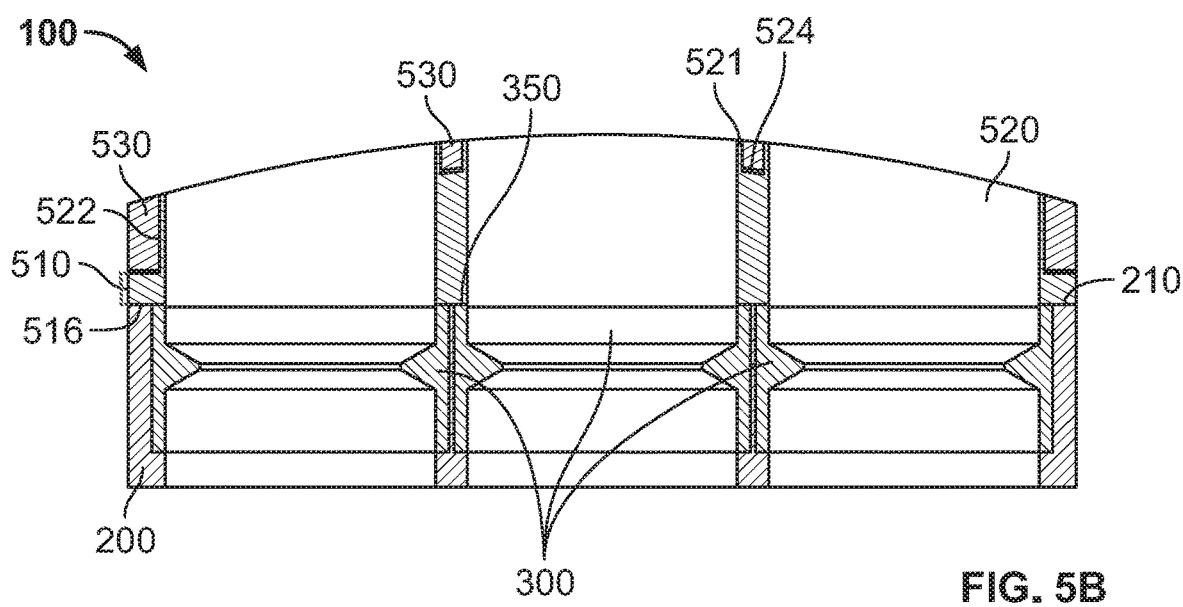
FIG. 5B depicts a side profile, cross-sectional view of the implant of FIG. 1 taken along a midline thereof.

As shown in FIG. 5B, recesses 524, which are located between adjacent cylindrical members 520, extend a first distance from terminal ends 521 of such cylindrical members. The magnitude of the first distance is smaller than a second distance 522, which extends from the terminal ends 521 of cylindrical members 520 to top surface 514 of plate 510 as seen adjacent to a radial edge of cap 502 in FIG. 5B. Bore walls of cylindrical members 520 have smooth inner and outer faces with a thickness therebetween, and are concentric about bore holes 302 of insert 300 and bores 220 of base 200. Thus, where bore holes 302 extend at a multitude of different angles, cylindrical members 520 would similarly extend at such angles so as to be concentric with its corresponding bore hole 302. As shown, a top end or second end of implant 100 is convex. In this regard, the magnitude of second distance 522 is smaller closer to the outer edges and larger as second distance 522 increases towards the center in order to conform to the convexity. The thicknesses of the walls of cylindrical members 520 are configured to be thick enough to provide sufficient support during the formation of crown 530 while being thin enough to maximize the amount of volume of crown 530 that can be formed on top of surface 514, as described below.

FIGS. 5A-B also depict crown or porous section 530. Crown 530 is preferably formed via additive manufacturing in conjunction with cap 502 such that when second section 500 is fully formed on inserts 300 and base 200, crown 530 is positioned atop of first surface 514 of plate 510 and fills in recesses 524 between cylindrical portions 520. In this regard, crown 530 comprises a portion of an outer surface of implant 100 so as to promote bone ingrowth therein. As shown, crown 530 defines a convex end surface 531 flush with top surface 521. However, it is envisioned that, in other embodiments, end surface 531 may be flat or concave depending on the particular implant and application.

While second section is described as having a non-porous cap and porous crown, it is contemplated that second section may be entirely porous. Alternatively, porous crown may connect directly to base and extend therefrom while solid cylindrical structures may be built upon inserts and joined with the porous structure via the additive manufacturing process.

Porous section 530 is comprised of a porous structure that includes a plurality of interconnected struts that define void-spaces or pores. In the embodiment depicted in FIG. 1, the porosity of the porous structure 530 may be about 10% to 90% with an average pore size of between 20-1000 microns. However, porous section 530 preferably includes a pore size of between 100 and 700 microns with a mean pore size of 400 to 500 microns and a mean porosity of 55% to 65%. Examples of such a porous structure are described in U.S. Pat. Nos. 9,456,901 and 9,135,374, which are incorporated by reference herein in their entirety.

As mentioned above, second section, which includes cap and crown, is additively manufactured on top of base 200 and inserts 300. Indeed, as described further below, base 200 may also be additively manufactured. In this regard, second section and base 200 may be formed layer-by-layer using an additive layer manufacturing (ALM), i.e., 3D printing, process so no separate connection mechanism is necessary to bring together second section and base 200. In some examples, ALM processes are powder-bed based and involve one or more of selective laser sintering (SLS), selective laser melting (SLM), and electron beam melting (EBM), as disclosed in U.S. Pat. Nos. 7,537,664; 8,728,387; 9,180,010; and 9,456,901 as well as U.S. Patent Publication No. 2006/0147332, each of which is hereby incorporated by reference in their entireties herein. Other methods of ALM, which can be used to form the herein described implant 100, include stereolithography (SLA), fused deposition modeling (FDM), and continuous liquid interface production (CLIP).

When employing powder-bed based technologies, articles are produced in layer-wise fashion according to a predetermined digital model of such articles by heating, e.g., using a laser or an electron beam, multiple layers of powder, which preferably may be a metallic powder, that are dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. The powder layers similarly may be heated with EBM technology. Additive manufacturing techniques such as the ALM processes described above may be employed to form the solid and porous layers and any other components, as applicable. In some instances, materials for one layer may be different than the materials for successive layers. This process allows for porous portions to have a full thickness extend through the crown. It also allows porous portions to be formed in locations impossible to reach by other methods. Moreover, it allows intricate structures to be formed.

Each of solid and porous layers of implant 100 may be constructed from biocompatible metals, such as but not limited to any one of or any combination of titanium and its alloys, stainless steel and its alloys, magnesium and its alloys, cobalt and its alloys including a cobalt chrome alloy, nickel and its alloys, silver, tantalum, and niobium, or biocompatible polymers, such as but not limited to any one of or any combination of polyethylene (PE) and variations thereof, polyetheretherketone (PEEK), polyetherketone (PEK), acrylonitrile butadiene styrene (ABS), silicone, and cross-linked polymers. In some arrangements, implant 100 may be made of certain other materials such as but not limited to bioabsorbable glass, ceramics, and biological active materials including collagen/cell matrices. In some arrangements, implant 100 may be made of a combination of any of these metals, polymers, and other materials. All constituent porous and solid portions of implant 100 may be a common material, such as one of those listed above, or different materials can be employed for each part. Particular combinations of materials and their use for specific parts of herein described implant 100 are a matter of design choice and may include the combination of different metals, different polymers, or metals combined with polymers. For example, the solid portions of implant 100 can be made from a metal while the porous portions may be made from a polymer.

However, due to the limitations of additive manufacturing, such as high resolution tolerances, inserts 300 are preferably made via alternative means that are capable of high resolution tolerances, such as via various forms of machining known in the art. However, inserts can also be made via casting, forging, molding, and the like. Thus, inserts 300 may be separately manufactured and assembled with base 200 to form partial construct 400, as shown in FIG. 4, prior to the formation of second section. In this regard, the method described below leverages the strengths of various means of manufacture to create a unified orthopedic device. It should also be understood that base 200, while being described herein as being additively manufactured, may be separately machined, cast, molded, forged, or the like and later brought together with inserts 300. Alternatively, inserts 300 may not be separately made. Instead, base 200 may be machined or otherwise manufactured such that protrusions 320 and bore holes 302 are formed from the same blank of material as base 200 thereby creating a monolithic structure without separate inserts 300.

In addition to that described above and illustrated in the figures, various other operations will now be described. It should be understood that the following operations do not have to be performed in the exact order described below. Instead, various steps may be handled in a different order or simultaneously. Steps may also be omitted or added unless otherwise stated therein.

Figure 6:
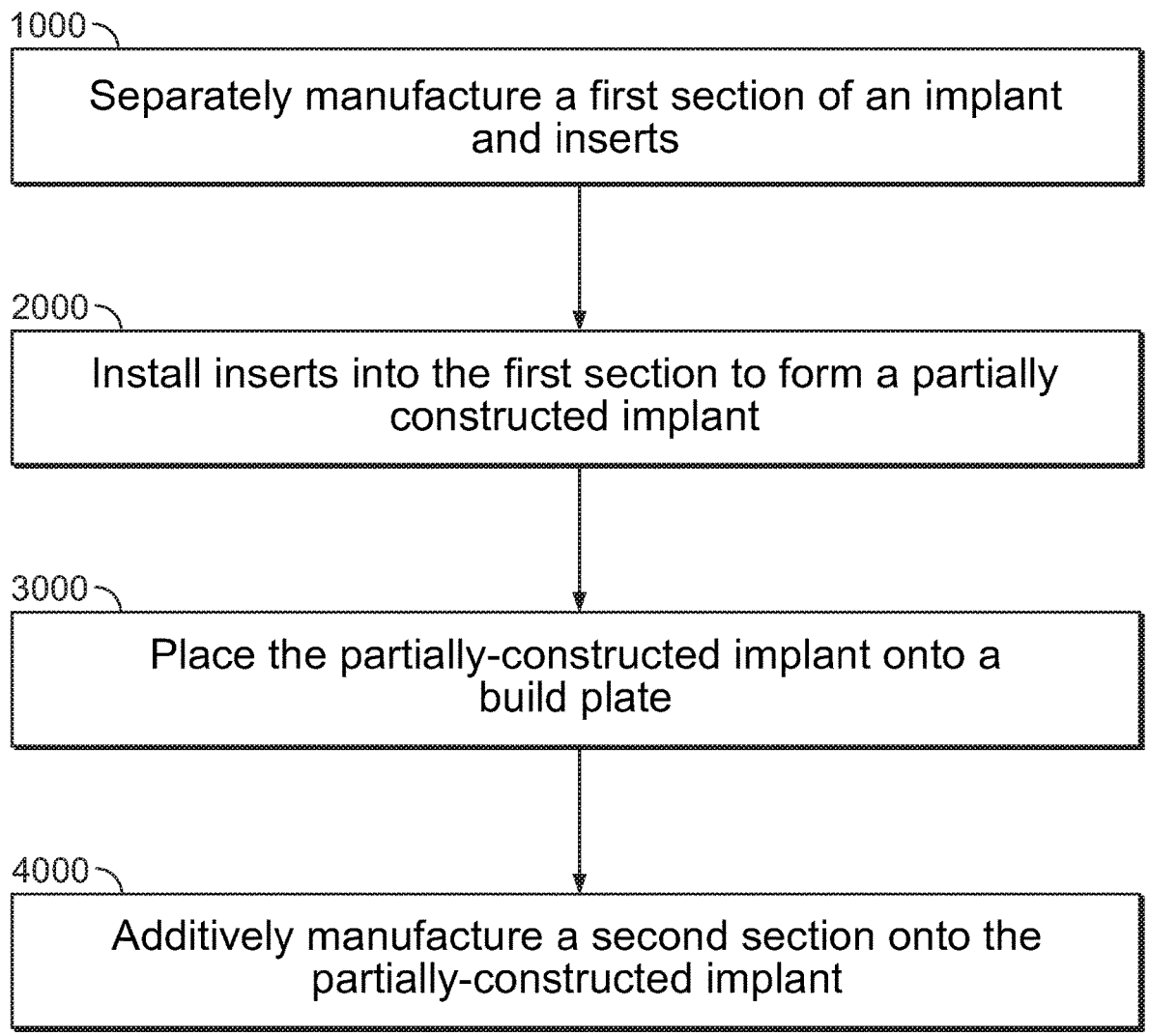
FIG. 6 is a flowchart of a method of manufacturing the implant according to one embodiment of the present invention.
Figure 7:
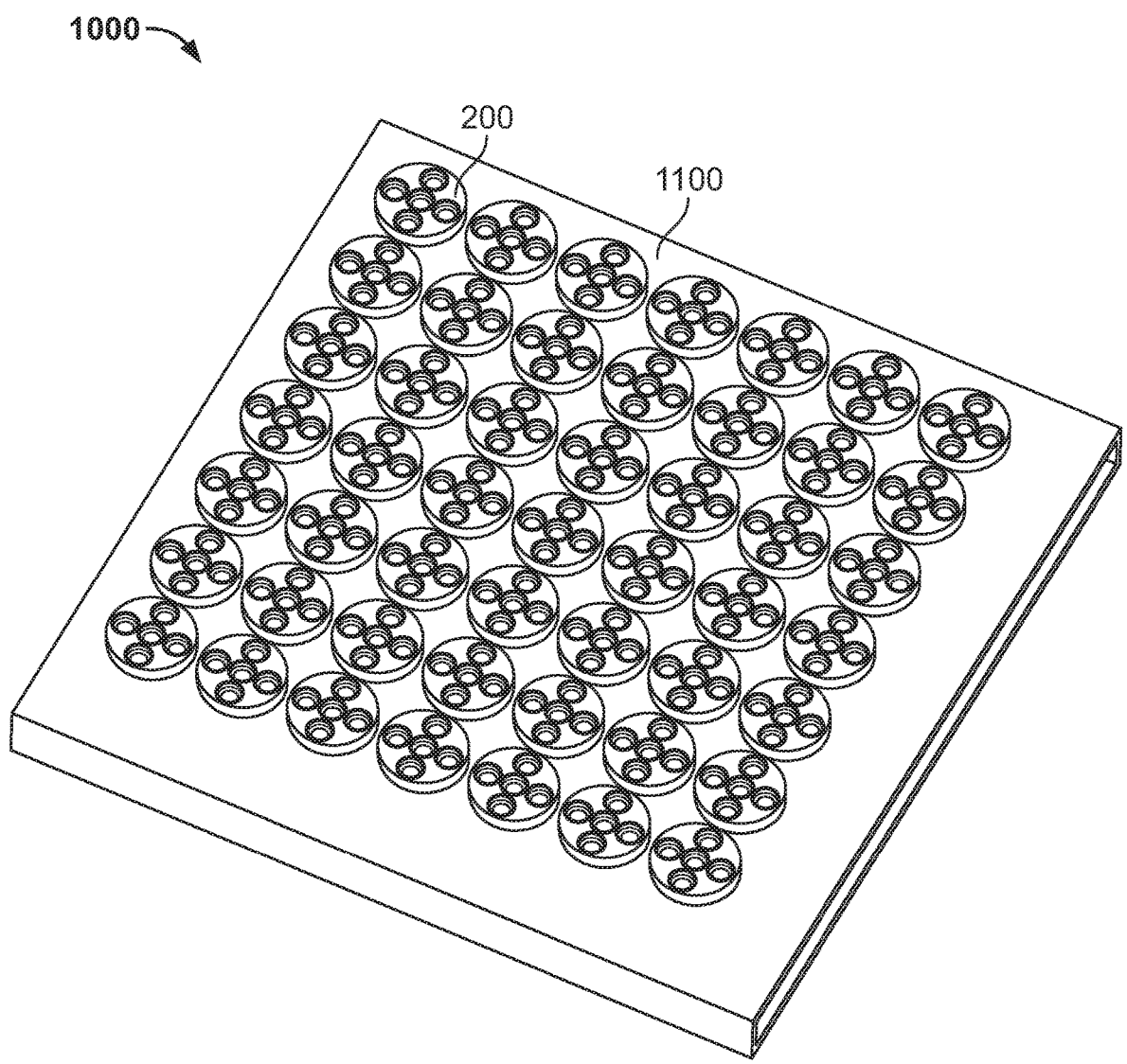
FIGS. 7-9 depict the method of manufacturing of FIG. 6.
Figure 8:
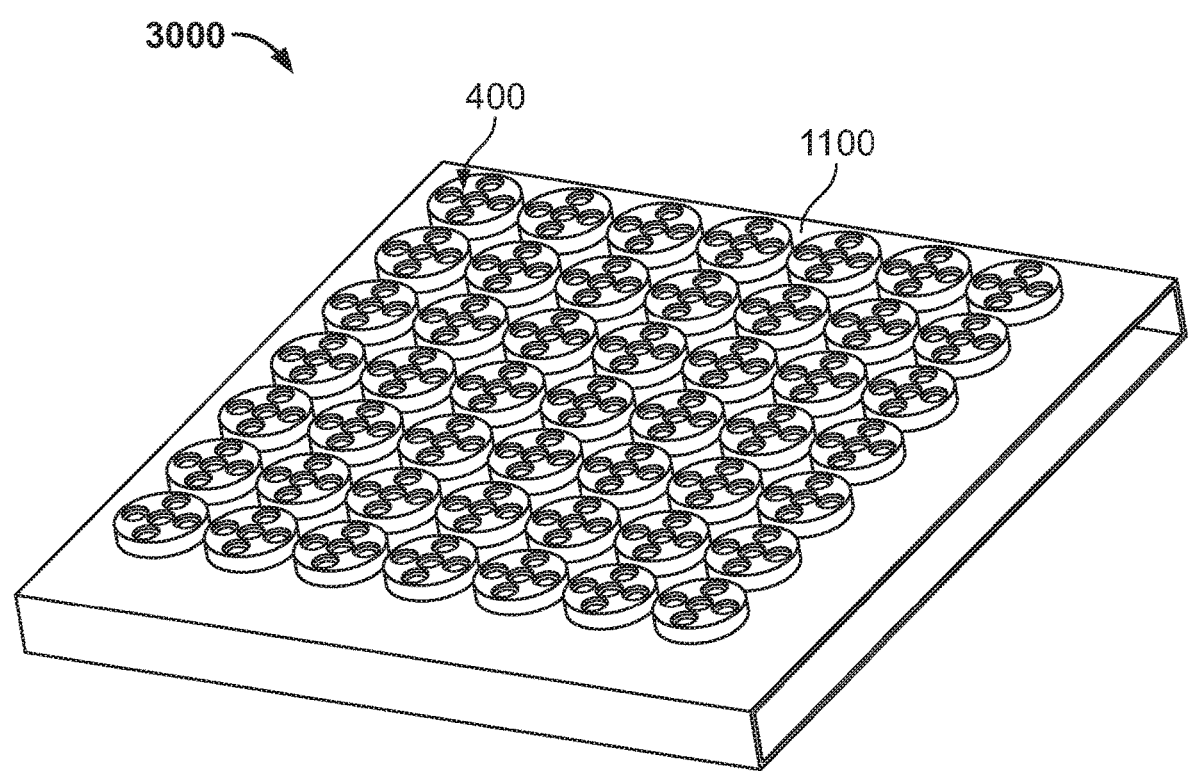
Figure 9:
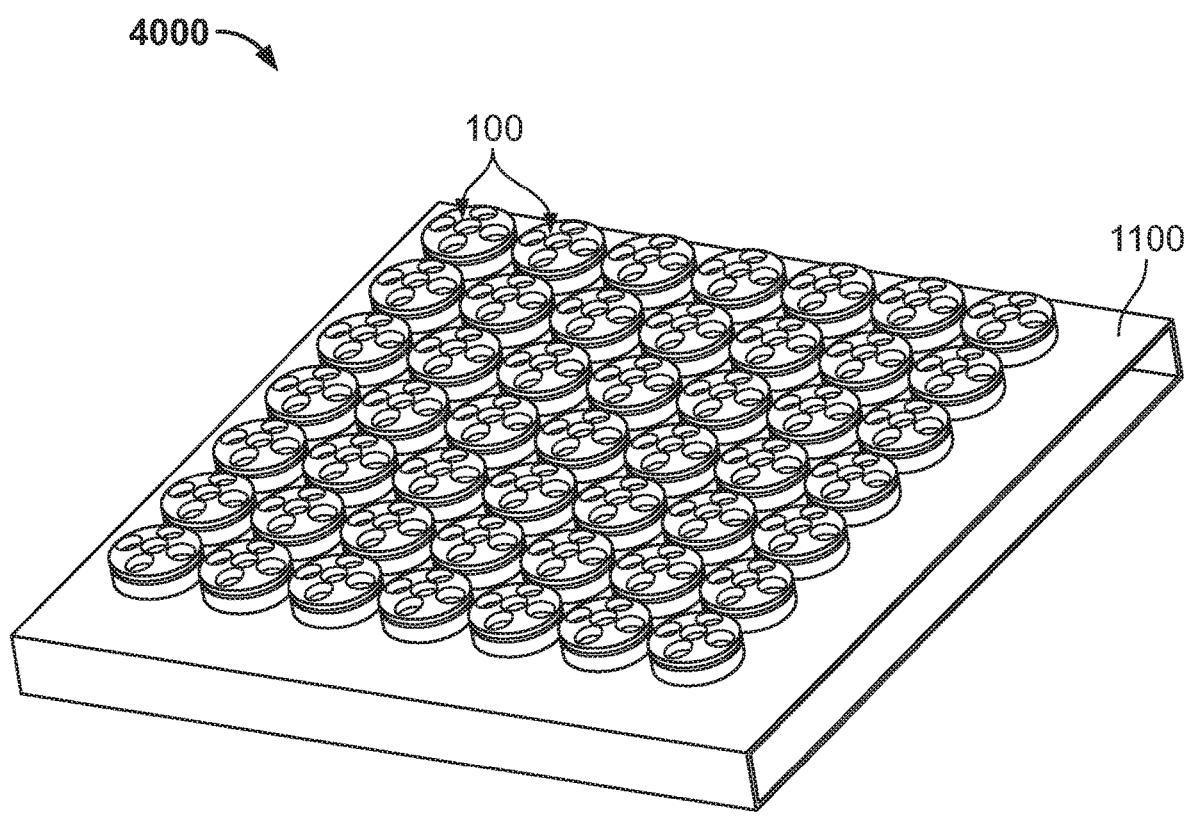

In one embodiment of the present disclosure, a method of manufacturing implant 100 is illustrated in the flowchart of FIG. 6 and various steps identified in the flowchart are depicted in FIGS. 7-9. In step 1000, as shown in FIG. 7, one or more bases 200 and inserts 300 are separately manufactured. In a preferred embodiment, bases 200 are manufactured by means of an additive manufacturing process on a build plate 1100. In this regard, bases 200 are built up layer by layer until fully formed. However, in alternative embodiments, it is envisioned that bases 200 are manufactured via other means, such as through machining, forging, casting, injection molding, or the like. In addition, inserts 300 are machined or otherwise separately manufactured, rather than additively manufactured. For instance, inserts 300 may have a tolerance level and/or surface finish that current additive manufacturing techniques have difficulty producing. In such a case, inserts 300 may be separately manufactured (e.g. machined) before being combined with base 200 in order to easily achieve the desired tolerances. Other forms of manufacturing that allow for this high degree of surface finish are also envisioned.

In step 2000, inserts 300 are installed within respective bores 220 of base 200 to form individual assemblies 400. In a preferred embodiment, this may involve individually removing base 200 from build plate 1100 before installing insert 300. Alternatively, it is envisioned that, in other embodiments, inserts 300 may be installed while base 200 is still on build plate 1100. Inserts 300 may additionally be secured to base 200 via welding or other means, such as fins extending from inserts 300, in order to prevent relative rotation of inserts within bores 220.

In step 3000, as shown in FIG. 8, assembly 400 is placed back into position for further additive manufacturing. Depending on how step 2000 was performed, the assembly 400 may be individually placed back onto build plate 1100, the build plate 1100 may be placed back into its original position, or some combination of both. For example, where each base 200 is removed from build plate 1100, they are returned to the same position or at least the same position occupied by a different base 200. In this regard, a first base 200 is built at a first position and at a first orientation on build plate 1100 and then removed to insert inserts 300 therein to form assembly 400. Thereafter, assembly 400 is returned to the first position and first orientation, or a second position and second orientation previously occupied by a second base 200. This allows the additive manufacturing machine to use positional coordinates of each base 200 relative to the build plate when building porous sections 530 thereon, as described below. However, each base 200 can be positioned in all new positions and orientations in which case the additive manufacturing machine may undergo a registration process prior to further additive manufacturing steps.

In step 4000, as shown in FIG. 9, second section 500 is additively manufactured on top of partially-constructed implant 400 to create implant 100. Thus, nonporous cap 502 and porous crown 530 are additively formed layer-by-layer on top of partially constructed implant 400. This may include depositing a metal powder or the like on top of base 200 and inserts 300 and then fusing the powder, via sintering, melting or the like, to base 200 and inserts 300. Based on the particular configuration of implant 100, as shown in FIGS. 5A and 5B, this may include the formation one or more nonporous layers on top of base 200 and inserts 300 to form plate 510. Subsequent layers may comprise both porous and non-porous structures so as to form cylindrical portions 520 and porous crown 530, respectively. In this regard, porous crown 530 and nonporous cap 502 are fused together to form a monolithic structure. Moreover, second section 500 is fused to base 200 and inserts 300. In this respect, inserts 300 are prohibited from rotating within base 200 and moving axially relative to base 200 and section 500.

It is envisioned that other intermediate or post-processing steps may be included in the above described manufacturing method. For example, intermediate steps may be performed on base 200 after base 200 is manufactured in step 1000 but before assembly or just after assembly with inserts 300. In addition, post-processing steps may be performed on implant 100 after step 4000. Such intermediate and post-processing steps may include, for example, removing surrounding powder, heat treatment (e.g., sintering), hot isostatic pressing, infiltration of other material, machining, surface treatment (e.g., sanding, polishing, or the like), and/or inspecting and testing. Additionally, in step 2000 and where base 200 is removed from build plate 1100, base 200 may be cleaned before installing inserts 300. Similarly, in step 300 and where assembly 400 is removed from base plate 1100, assembly 400 may be cleaned before installing inserts 300. This cleaning step may involve rinsing the parts with water, chemical solutions or the like. Alternatively cleaning may involve vacuuming or blowing the debris away.

Although the method of manufacturing described in FIGS. 6-9 is described to create a medical implant, it is envisioned that the method of manufacturing described herein may be performed for any medical device that has multiple parts, where such parts have differing characteristics that would be best produced by different manufacturing processes.

Figure 10:
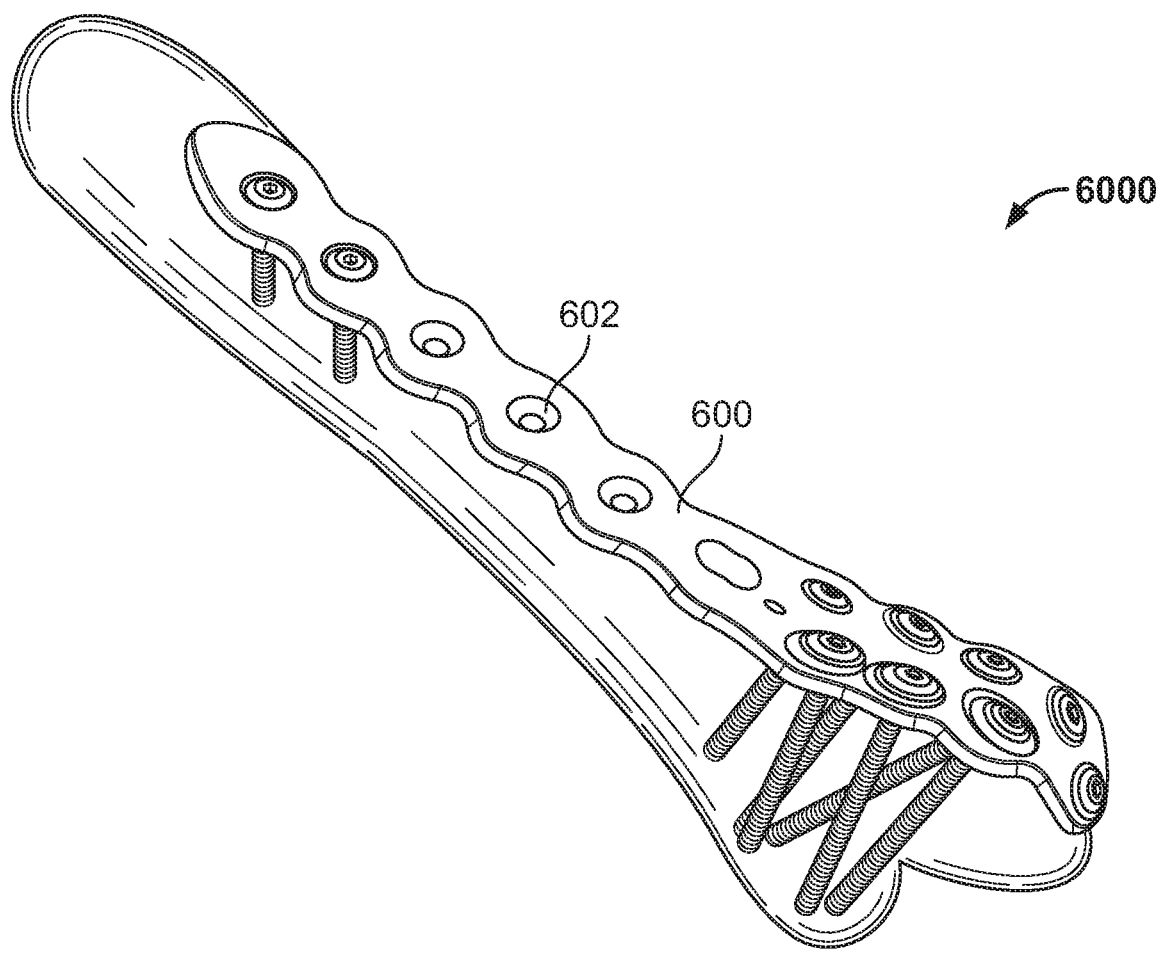
FIG. 10 is a perspective view of a bone plate according to an embodiment of the present invention connected to a bone.

FIG. 10 depicts another exemplary device that may be manufactured by the aforementioned processes. In particular, a bone plate 6000 is depicted. Bone plate 6000 includes a plate body 600 and a plurality of screw holes 602 extending therethrough. Bone plates typically have unique geometries that allow them to conform to a particular bone. In this regard, bone plates may be advantageously manufactured via an additive manufacturing process which can easily and repeatedly produce such geometries. Moreover, additive manufacturing of bone plates allows for such bone plates to be patient specific as a patient's particular bone structure may be imaged via medical imaging technology and input into additive manufacturing software so that the geometries of a patient specific bone plate can be easily determined. However, as discussed above, tight tolerances may be difficult to achieve via additive manufacturing with respect to the screw openings of such bone plates. As such, separate inserts, such as insert 300, may be manufactured via machining or otherwise and connected to plate body 600 during an additive manufacturing process to achieve the desired results. It is noted that bone plates typically do not utilize porous surfaces as bone ingrowth is typically not desirable or necessary. However, additive manufacturing is still advantageous and may be used to create an entirely solid (i.e., nonporous) plate body 600 with the added advantage of separately manufactured inserts that have the desired tolerances for screw openings 602.

Thus, in an embodiment of a method of manufacture, a first solid section may be produced via additive manufacturing or some other means of manufacturing, such as forging, casting, molding, and machining. Separately manufactured inserts with the desired tolerances may then be inserted into bores formed in the first solid section. Thereafter, a second solid section may be additively manufactured atop of the base and inserts so as to trap the inserts between both layers and lock them to bone plate body 600.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of manufacturing an implant comprising:
    manufacturing a first portion;
    coupling an insert with the first portion to form a combined first portion and insert assembly; and
    additively manufacturing a second portion directly on the assembly after the coupling step.

2. The method of claim 1, further comprising separately manufacturing the insert from the first portion via one of machining, molding, casting, and forging.

3. The method of claim 1, wherein coupling the insert with the first portion includes inserting the insert into a bore of the first portion by one of press-fit and threading.

4. The method of claim 1, wherein the second portion comprises a porous structure having a porosity of 10% to 90%.

5. The method of claim 4, wherein the first portion comprises a solid structure.

6. The method of claim 1, wherein manufacturing the first portion includes additively manufacturing the first portion on a build plate, and the method further comprises removing the first portion from the build plate prior to coupling the insert to the first portion.

7. The method of claim 6, further comprising placing the combined first portion and insert assembly onto the build plate prior to the step of additively manufacturing the second portion.

8. The method of claim 7, wherein manufacturing the first portion includes additively manufacturing the first portion on the build plate such that the first portion occupies a first position on the build plate, and the placing step includes placing the first portion and insert assembly in the first position on the build plate.

9. The method of claim 1, wherein additively manufacturing the first portion is performed on a build plate located at a first location, and the method further comprises transporting the build plate including the first portion thereon from the first location to a second location, the coupling step being performed at the second location.

10. The method of claim 1, wherein additively manufacturing the second portion is performed over at least a portion of the insert such that the insert is at least partially disposed beneath the second portion thereby securing the insert to the first portion.

11. The implant of claim 1, wherein the second portion is fused to the assembly.

* * * * *